(12) United States Patent
Wu et al.

(10) Patent No.: US 9,025,815 B2
(45) Date of Patent: *May 5, 2015

(54) SYSTEM AND METHOD FOR MULTI-MATERIAL CORRECTION OF IMAGE DATA

(71) Applicant: General Electric Company, Schenectady, NY (US)

(72) Inventors: Xiaoye Wu, Rexford, NY (US); Jiang Hsieh, Brookfield, WI (US); Paavana Sainath, Oconomowoc, WI (US); Dan Xu, Aurora, IL (US); Yannan Jin, Schenectady, NY (US); Girijesh Kumar Yadava, Waukesha, WI (US); Adam Israel Cohen, Milwaukee, WI (US); Hewei Gao, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/332,020

(22) Filed: Jul. 15, 2014

(65) Prior Publication Data
US 2014/0328448 A1 Nov. 6, 2014

Related U.S. Application Data

(63) Continuation of application No. 13/677,010, filed on Nov. 14, 2012, now Pat. No. 8,811,709.

(51) Int. Cl.
*G06K 9/00* (2006.01)
*A61B 6/03* (2006.01)
(Continued)

(52) U.S. Cl.
CPC ........... *A61B 6/03* (2013.01); *G06T 7/0012* (2013.01); *G06T 11/008* (2013.01); *G06T 2211/408* (2013.01)

(58) Field of Classification Search
USPC ......... 382/100, 103, 128–134, 154, 162, 168, 382/173, 181, 224, 232, 254, 274, 275, 276, 382/305, 312; 378/4, 19, 21, 5; 375/5
See application file for complete search history.

(56) References Cited

U.S. PATENT DOCUMENTS 5,907,593 A * 5/1999 Hsieh et al. .................. 378/4
7,298,812 B2 * 11/2007 Tkaczyk et al. ............... 378/5
(Continued)

OTHER PUBLICATIONS

Kasperl et al., "Computed Tomography Metrology in Industrial Research & Development", International Symposium on NDT in Aerospace, pp. 1-8, Dec. 2008.
(Continued)

*Primary Examiner* — Seyed Azarian
(74) *Attorney, Agent, or Firm* — Robert M. McCarthy

(57) ABSTRACT

A method is provided. The method includes acquiring projection data of an object from a plurality of pixels, reconstructing the acquired projection data from the plurality of pixels into a reconstructed image, performing material characterization and decomposition of an image volume of the reconstructed image to reduce a number of materials analyzed in the image volume to two basis materials. The method also includes generating a re-mapped image volume for at least one basis material of the two basis materials, and performing forward projection on at least the re-mapped image volume for the at least one basis material to produce a material-based projection. The method further includes generating multi-material corrected projections based on the material-based projection and a total projection attenuated by the object, which represents both of the two basis materials, wherein the multi-material corrected projections include linearized projections.

26 Claims, 4 Drawing Sheets

(51) Int. Cl.
*G06T 7/00* (2006.01)
*G06T 11/00* (2006.01)
*A61B 6/00* (2006.01)

(56) References Cited

U.S. PATENT DOCUMENTS

| | | | |
|---|---|---|---|
| 7,315,604 | B2 | 1/2008 | Raupach |
| 7,391,844 | B2 | 6/2008 | Wu et al. |
| 7,444,010 | B2 | 10/2008 | De Man |
| 7,466,793 | B2 * | 12/2008 | Wu et al. .................. 378/19 |
| 7,747,057 | B2 * | 6/2010 | Wu et al. .................. 382/131 |
| 2009/0214095 | A1 | 8/2009 | Wu et al. |
| 2011/0044559 | A1 | 2/2011 | Erhard et al. |
| 2011/0052022 | A1 * | 3/2011 | Xu et al. .................. 382/131 |

OTHER PUBLICATIONS

Stenner et al., "Dynamic iterative beam hardening correction (DIBHC) for an optimized assessment of cardiac perfusion in ECG-correlated CT", Nuclear Science Symposium Conference Record (NSS/MIC), 2009 IEEE, pp. 3523-3530, 2009.

Dembowski., "IAR—Artifact Reductions in Computed Tomography", Fraunhofer EZRT, pp. 1-6, Apr. 2010.

Krumm et al., "Beam hardening correction of multi-material objects", 10th European Conference on Non-Destructive Testing, ECNDT, pp. 1-7, 2010.

* cited by examiner

SYSTEM AND METHOD FOR MULTI-MATERIAL CORRECTION OF IMAGE DATA

CROSS-REFERENCE TO RELATED APPLICATIONS

This application is a continuation of patent application Ser. No. 13/677,010, entitled "System and Method for Multi-Material Correction of Image Data," filed Nov. 14, 2012, which is herein incorporated by reference in its entirety for all purposes.

BACKGROUND

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In CT systems a detector array, including a series of detector elements, produces similar signals through various positions as a gantry is displaced around a patient.

In the images produced by such systems, it may be possible to identify and examine the internal structures and organs within a patient's body. However, the produced images may also include artifacts that adversely affect the quality of the images due to a variety of factors. For example, these factors may include beam hardening for non-water materials, heel-effect related spectral variation in wide cone CT systems, bone induced spectral (BIS) due to detection variation of different detector pixels coupled to spectral changes attenuated by bone or other non-water materials, and other factors. Present techniques to correct for these artifacts are empirically based and inaccurate.

BRIEF DESCRIPTION

In accordance with a first embodiment, a method is provided. The method includes acquiring projection data of an object from a plurality of pixels, reconstructing the acquired projection data from the plurality of pixels into a reconstructed image, performing material characterization and decomposition of an image volume of the reconstructed image to reduce a number of materials analyzed in the image volume to two basis materials. The method also includes generating a re-mapped image volume for at least one basis material of the two basis materials, and performing forward projection on at least the re-mapped image volume for the at least one basis material to produce a material-based projection. The method further includes generating multi-material corrected projections based on the material-based projection and a total projection attenuated by the object, which represents both of the two basis materials, wherein the multi-material corrected projections include linearized projections.

In accordance with a second embodiment, one or more non-transitory computer readable media are provided. The computer-readable media encode one or more processor-executable routines. The one or more routines, when executed by a processor, cause acts to be performed including: acquiring projection data of an object from a plurality of pixels, reconstructing the acquired projection data from the plurality of pixels into a reconstructed image, and performing material characterization and decomposition of the image volume of the reconstructed image to reduce a number of materials analyzed in the image volume to two basis materials. The acts to be performed also include generating a re-mapped image volume for at least one basis material of the two basis materials, and performing forward projection on at least the re-mapped image volume for the at least one basis material to produce a material-based projection. The acts to be performed further include generating multi-material corrected projections based on the material-based projection and a spectrally corrected total raw projection attenuated by the object, which represents both of the two basis materials, wherein the multi-material corrected projections include linearized projections.

In accordance with a third embodiment, a system is provided. The system includes a memory structure encoding one or more processor-executable routines. The routines, when executed, cause acts to be performed including: acquiring projection data of an object from a plurality of pixels, reconstructing the acquired projection data from the plurality of pixels into a reconstructed image, performing material characterization and decomposition of an image volume of the reconstructed image to reduce a number of materials analyzed in the image volume to two basis materials, iodine and water. The acts to be performed also include generating a re-mapped image volume for at least iodine, and performing forward projection on at least the re-mapped image volume for iodine to produce an iodine-based projection. The acts to be performed further include generating multi-material corrected projections based the iodine-based projection and a spectrally corrected total raw projection attenuated by the object, which represents both water and iodine, wherein the multi-material corrected projections include linearized projections. The system also includes a processing component configured to access and execute the one or more routines encoded by the memory structure.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
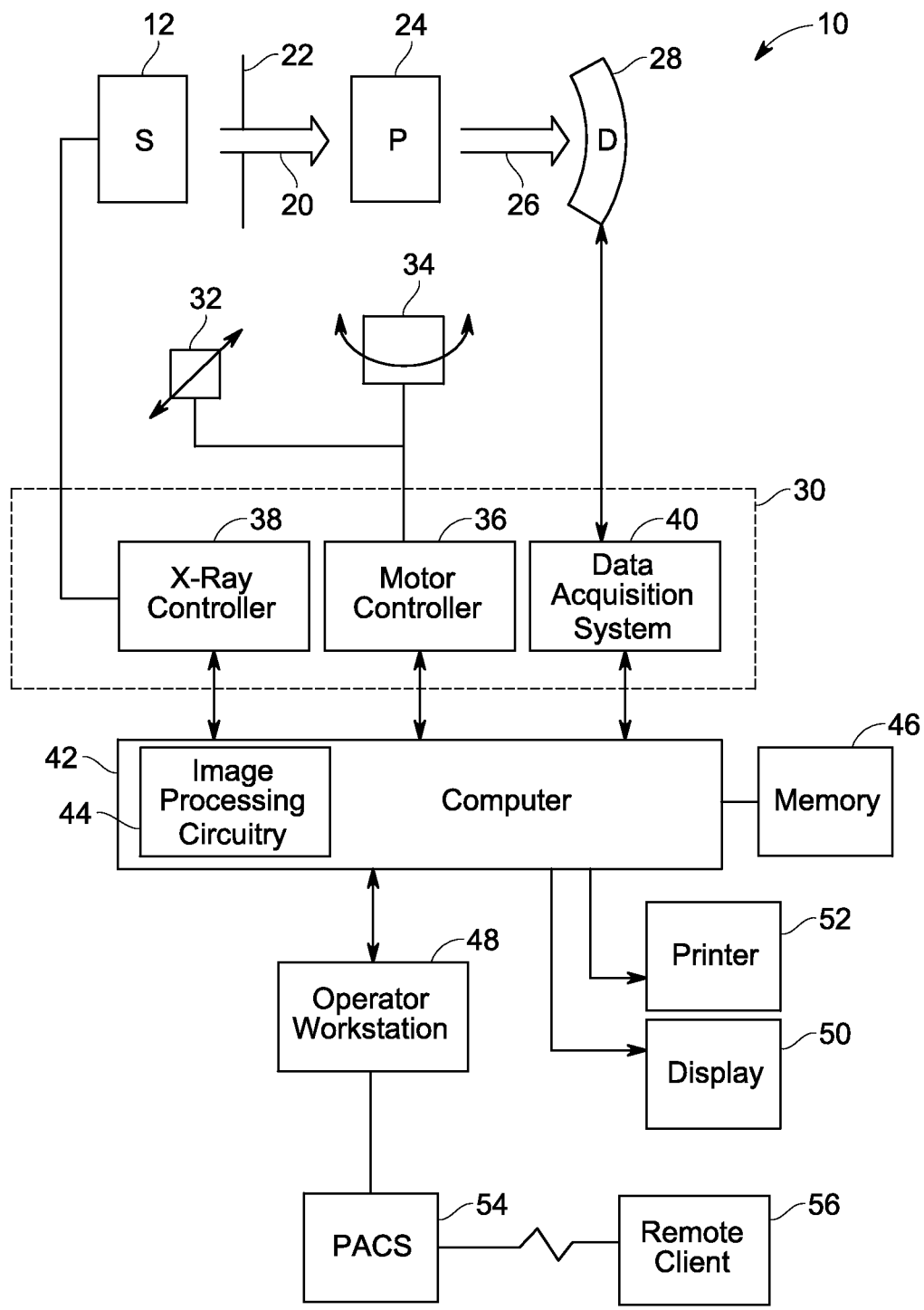
FIG. 1 is a schematic illustration of an embodiment of a computed tomography (CT) system configured to acquire CT images of a patient and to process the images in accordance with aspects of the present disclosure.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

Tissue characterization or classification may be desirable in various clinical contexts to assess the tissue being characterized for pathological conditions and/or to assess the tissue for the presence of various elements, chemicals or molecules of interest. However, tissue characterization in imaging studies, such as using computed tomography (CT), may be problematic due to the presence of artifacts present within the reconstructed images. These artifacts may be present due to a variety of sources. For instance, due to the nature of a polychromatic X-ray beam produced by the Bremsstrahlung process, the beam attenuated by different materials of an imaged subject will result in different exit beam spectra. The effect of the polychromatic nature of the input X-ray spectra and the energy-dependent nature of material attenuation by different materials induces "beam hardening" artifacts in the reconstructed image. In addition, the mean value of a given material is not constant. For example, presently the CT value of a non-water material is a function of the incident beam, location of the materials, type of reconstruction due to weighting, and adjacent materials around a region of interest (ROI). However, from a physics point of view, the presence of the beam hardening artifact is due to a single reason, the measured projections of a given type of material is not linearly proportional to the length of the material at different view angles.

Further factors also result in artifacts in the reconstructed images. For example, the "heel-effect" causes incident beam spectrum variation inside a wide cone angle, especially a beam with a few degrees take-off angle from the anode. The heel-effect results in different mean values of non-water materials across the cone angle. Another factor is due to the detection system in any clinical CT system not being perfect. For example, each detector pixel might have a slightly different response to given incident spectrum, resulting in differential errors in detection when the incident beam is not purely water-attenuated, causing a bone-induced spectral (BIS) artifact. Typically, iterative bone option (IBO) and BIS correction techniques used to correct these artifacts are empirically based and/or subject to error.

As discussed herein, in various implementations, a multi-material correction (MMC) approach is employed to compensate for artifacts within the reconstructed images. In particular, the MMC approach (e.g., algorithm) is designed to deal with the different sources of beam-hardening related issues described above with a single linearization correction to minimize artifacts that are not corrected by water-based spectral calibration and correction. The MMC approach is based on the underlying physics model, as opposed to being empirically based. In addition, the MMC approach linearizes the detection of all the materials present to eliminate beam hardening from its root cause, regardless of the material type, thus, resulting in more accurate and consistent CT values of bone, soft tissue, and contrast agent for better clinical diagnosis. Thus, the MMC approach minimizes the beam-hardening artifacts in the images that originate from bone, contrast agent, and metal implants. Additional direct clinical benefits due to the MMC approach include improved image quality, better differentiation between cysts and metastases, better delineation of bone-brain interface and accurate contrast measurement in CT perfusion. Further, the value of the contrast agent or bone can be corrected to be only kVp dependent, or more precisely, effective keV dependent, which is close to offering a monochromatic beam. Yet further, in contrast to the current techniques used with clinical CT systems, the MMC approach is not dependent on patient size or the location of the region-of-interest (ROI). Thus, the MMC approach may provide a technique for providing accurate CT values for contrast agent and bone.

With the foregoing discussion in mind, FIG. 1 illustrates an embodiment of an imaging system 10 for acquiring and processing image data in accordance with aspects of the present disclosure. In the illustrated embodiment, system 10 is a computed tomography (CT) system designed to acquire X-ray projection data, to reconstruct the projection data into a tomographic image, and to process the image data for display and analysis. The CT imaging system 10 includes an X-ray source 12. As discussed in detail herein, the source 12 may include one or more X-ray sources, such as an X-ray tube or solid state emission structures. The X-ray source 12, in accordance with present embodiments, is configured to emit an X-ray beam 20 at one or more energies. Although the following techniques discussed below utilize the emission of the beam at a single emission spectrum, the same techniques may be applied for the emission of the beam at two or more energies, although single-energy embodiments are discussed herein to simplify explanation. For example, the X-ray source 12 may be configured to switch between relatively low energy polychromatic emission spectra (e.g., at about 80 kVp) and relatively high energy polychromatic emission spectra (e.g., at about 140 kVp). Also, the X-ray source 12 may emit at polychromatic spectra localized around energy levels (i.e., kVp ranges) other than those listed herein (e.g., 100 kVP, 120 kVP, etc.). Indeed, selection of the respective energy levels for emission may be based, at least in part, on the anatomy being imaged.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another. The X-ray controller 38 is configured to control the source 12 to emit X-rays at a single polychromatic energy spectrum in an image acquisition sequence to acquire a single energy dataset. In certain embodiments, the X-ray controller 38 may be configured to provide fast-kVp switching of the X-ray source 12 so as to rapidly switch the source 12 to emit X-rays at the respective different polychromatic energy spectra in succession during an image acquisition session. For example, in a dual-energy imaging context, the X-ray controller 38 may operate the X-ray source 12 so that the X-ray source 12 alternately emits X-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, the fast-kVp switching operation performed by the X-ray controller 38 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

As noted above, the X-ray source 12 may be configured to emit X-rays at one or more energy spectra. Though such emissions may be generally described or discussed as being at a particular energy (e.g., 80 kVp, 140 kVp, and so forth), the respective X-ray emissions at a given energy are actually along a continuum or spectrum and may, therefore, constitute a polychromatic emission centered at, or having a peak strength at, the target energy.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein (e.g., performance of MMC).

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Keeping in mind the operation of the system 10 and, specifically, the X-ray source 12 discussed above with respect to FIG. 1, FIG. 2 illustrates a process flow diagram of an embodiment of a method 58 for performing MMC on projection data (e.g., datasets). Any suitable application-specific or general-purpose computer having a memory and processor may perform some or all of the steps of the method 58. By way of example, as noted above with respect to FIG. 1, the computer 42 and associated memory 46 may be configured to perform the method 58. For example, the memory 46, which may be any tangible, non-transitory, machine-readable medium (e.g., an optical disc, solid state device, chip, firmware), may store one or more sets of instructions that are executable by a processor of the computer 42 to perform the steps of method 58. In accordance with present embodiments, the processor, in performing method 58, may generate one or more images corrected via MMC.

Figure 2:
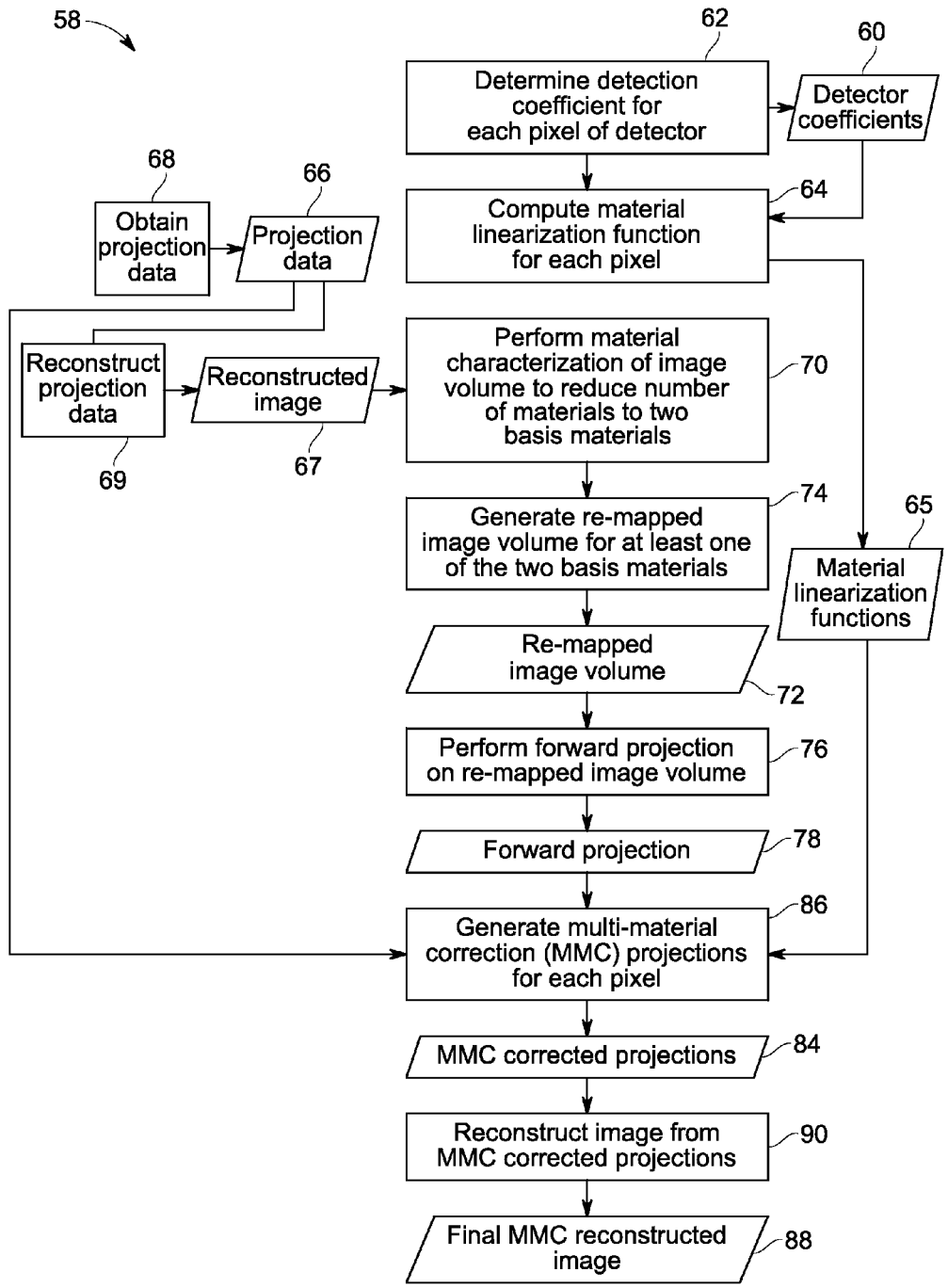
FIG. 2 is a process flow diagram of an embodiment of a method for performing multi-material correction on projection data.

Turning to FIG. 2, in the depicted implementation, the method 58 includes determining detection coefficients 60 for each pixel of the detector 28 (block 62). The detection coefficients 60 are only obtained once for each pixel and may be used for subsequent scans. The detection coefficients 60 are a function of the incident photon energy of each individual pixel. The detection coefficients 60 are captured from the data of 4 kVp air scans during spectral calibration. The detection coefficients enable the modeling of the detector signals. The detection coefficient 60 of pixel i is expressed in polynomial form in the following equation:

$$\epsilon(E,i)=\Sigma_0^{N-1} X_n(i) E^n, \quad (1)$$

where $\epsilon(E, i)$ represents the detection coefficient, E represents the photon energy, i represents the pixel index, $X_n(i)$ represents detection coefficients expressed in polynomial form, and N represents the number of kVp air scans during the spectral calibration. N is based on the number of kVp stations. For example, N may range from 4 to 5. The detection efficiency factor may depend on a number of factors such as different kVps and different filtrations. In certain embodiments, the $X_n(i)$ values may be stored, e.g., in memory 46, for use in MMC.

The detection coefficients 60 are utilized in computing a material linearization function (e.g., mapping function) 65 or beam hardening projection error for each pixel (block 64) using projections synthesized through system modeling as described in greater detail below. The mapping function 65 for each pixel is designed to linearize material projections for the respective pixel. In general, MMC is designed to re-map the detected signals so that the signals are all linearly proportional to each of the material's length with proper slope. The slope is a fixed value for each individual material that does not change from view to view. The slope assigned to each material can be any value in principle. But in practice, it should be very close to the attenuation coefficient at the effective energy (i.e., keV) of the beam. This keeps the correction small enough that the original noise is maintained and, thus, is more forgivable to errors in the material segmentation and characterization. As mentioned above, the mapping function for MMC is based on individual pixels. This individual pixel-based approach removes general physics beam hardening and variation in detector spectral response or absorption. As described in greater detail below, the mapping function 65 is generated based on two basis materials (e.g., water and iodine) in one embodiment. Other basis material pairs may be chosen from other materials such as calcium, metal, and bone. The use of two basis materials enables a complex body composition to be simplified into two components. This reduces the need for forward projections for other materials (i.e., those not selected as the basis materials), while also reducing the complexity of the mapping function.

After determining the mapping function for each pixel, the method 58 includes obtaining projection data 66 (e.g., datasets) (block 68), for example, by acquiring the projection data 66 via the CT system 10 described above. The method 58 also includes reconstructing the projection data 66 from the plurality of pixels into a reconstructed image 67 (e.g., full field of view (FOV) reconstructed image) (block 69). The method 58 includes performing material characterization on an image volume (e.g., voxel) of the reconstructed image (block 70) to reduce a number of materials analyzed in each pixel to two basis materials (e.g., iodine and water). In the absence of k-edge materials in an object to be imaged, the object can be analyzed as a combination of two basis materials (e.g., iodine and water) from the physics point of view. In general, there are four distinct materials in a human body: soft tissue, bone, iodine, and metal implants. Also, if calcium is dense enough, it can approximately be considered as cortical bone. Using this theory, bone and metal are represented by water and iodine, and the human body may be described by a two-material system. As a result beam hardening is completely determined by the combination of two material projections. The material characterization enables the transformation of multiple materials (e.g., metal, bone, etc.) in the image volume into proper representations of two basis materials (e.g., water and iodine). As described in greater detail below, the material characterization may include performing material segmentation and inverse basis material decomposition.

The method 58 further includes generating a remapped image volume 72 (e.g., material-based projection from a re-mapped pixel) (block 74) for at least one basis material (e.g., iodine) of the two basis materials (e.g., iodine and water). In certain embodiments, remapped projections 72 may be obtained for both basis materials (e.g., iodine and water). To utilize MMC, projections involving two basis materials are needed. For example, the projections involving the two basis materials include a total projection (e.g., water and iodine) attenuated by the object, which also represents both basis materials, and a projection contributed by one of the two basis materials (e.g., iodine) that represents the sums of the equivalent portions of each of the materials (e.g., non-water materials) that is not included in the other basis material of the basis material pair. The method 58 yet further includes performing forward projection on the re-mapped image volume 72 (block 76) to generate a forward projection 78 for at least one basis material (e.g., iodine) to produce a material-based (e.g., iodine-based) projection. Typically, a forward projection is not necessary for the total projection since the total projection from the measurement (i.e., projection data 66) already exists. Thus, only a single forward projection is required. In certain embodiments, forward projections may be performed on both a re-mapped total projection and the re-mapped projection of the projection contributed by one of the two basis materials (e.g., iodine). The image volume is forward-projected using the exact system geometry, and the forward projections are interpolated into the same ray directions and the same number of views as the measured projections (e.g., projection data 66) by the detection system, which results in paired data projection sets.

The method 58 includes generating MMC corrected projections 84 (e.g., linearized projections) for each pixel based on the material-based projection 78 and initial total projection (e.g., projection data 66) representing attenuation through both of the two basis materials (e.g., iodine and water). In particular, the MMC corrected projections 84 may be based on a summation of the initial total projection and the material linearization function 65 or beam hardening projection error (block 86). In certain embodiments, the initial total projection and the linearization function 65 or beam hardening projection error may be subtracted from each other. The linearization function 65 is based on the values for the material-based projection 78 and the total initial total projection. In certain embodiments, the initial total projection may be a spectrally corrected total raw projection. The method 58 further includes reconstructing a final MMC reconstructed image 88 from the MMC corrected projections 84 (block 90).

Figure 3:
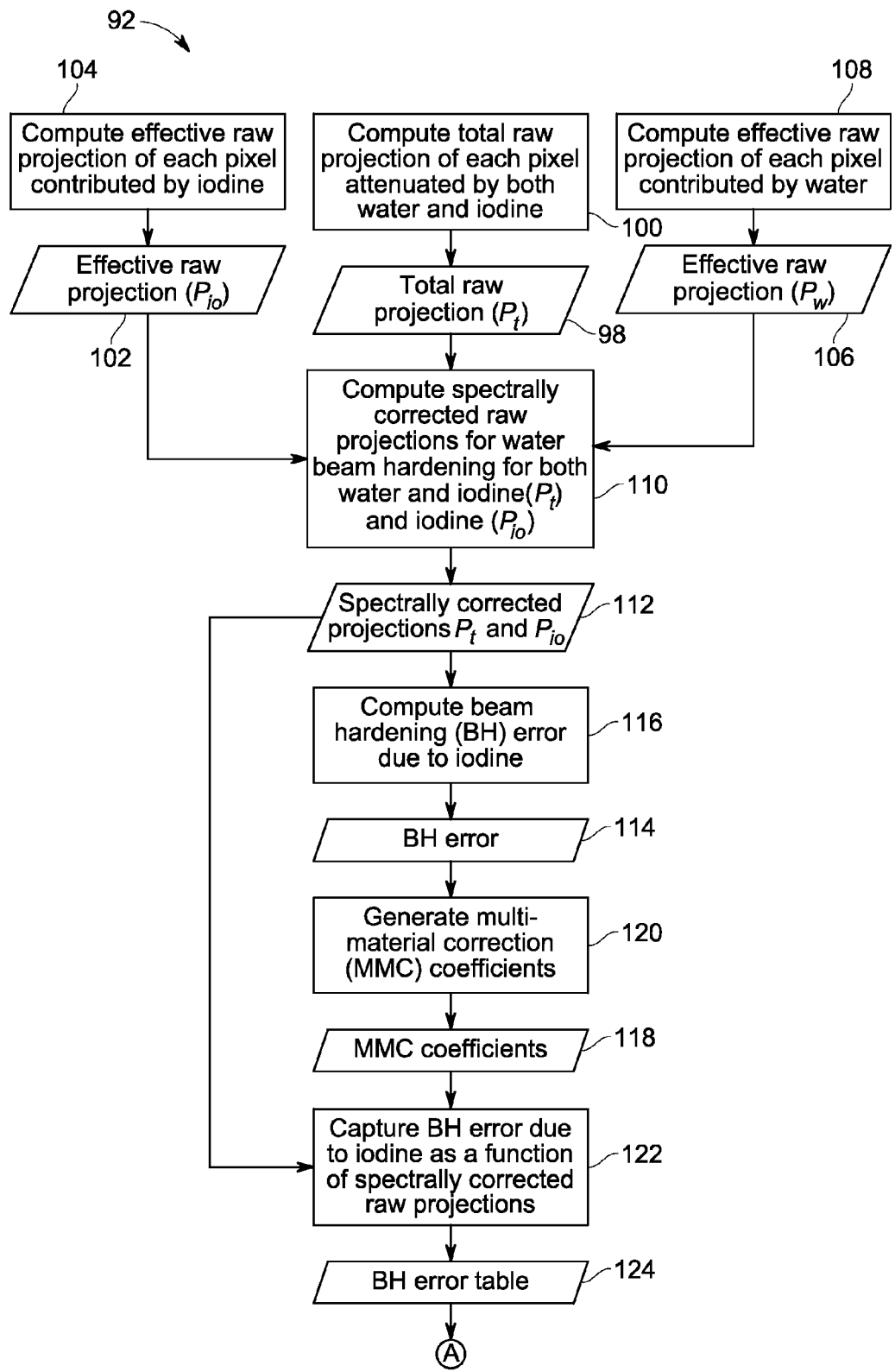
FIG. 3 is a detailed process flow diagram of an embodiment of a method for performing multi-material correction on projection data that utilizes water and iodine as basis materials.
Figure 4:
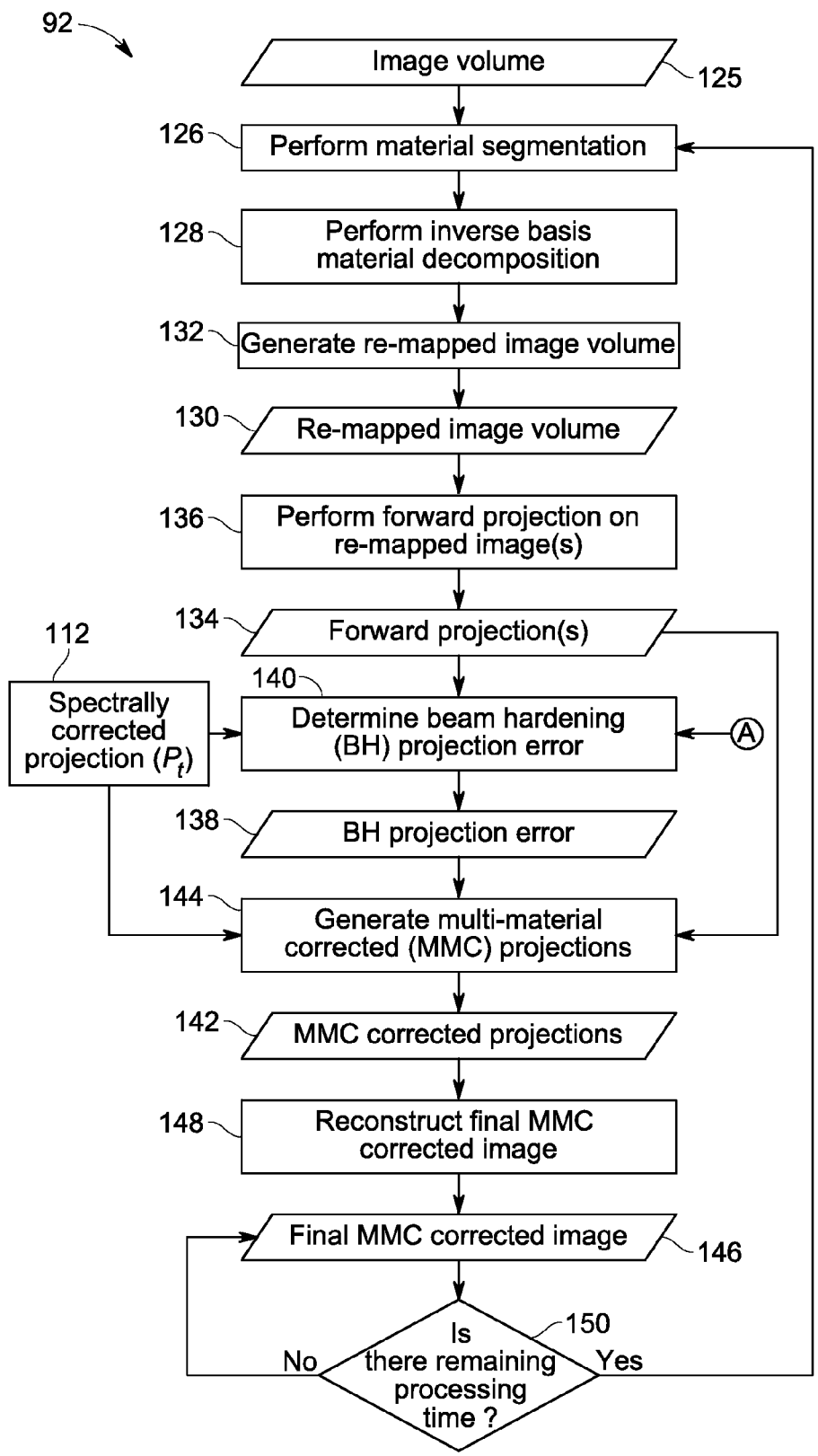
FIG. 4 is a continuation of the method of FIG. 3.

FIGS. 3 and 4 illustrate a detailed process flow diagram of an embodiment of a method 92 for performing MMC on projection data that utilizes iodine and water as the two basis materials. As noted above, other materials may be used for the basis material pair. Any suitable application-specific or general-purpose computer having a memory and processor may perform some or all of the steps of the method 92. By way of example, as noted above with respect to FIG. 1, the computer 42 and associated memory 46 may be configured to perform the method 92. For example, the memory 46, which may be any tangible, non-transitory, machine-readable medium (e.g., an optical disc, solid state device, chip, firmware), may store one or more sets of instructions that are executable by a processor of the computer 42 to perform the steps of method 92. In accordance with present embodiments, the processor, in performing method 92, may generate one or more images corrected via MMC.

It should be noted, the method 92 may include determining detection coefficients for each pixel of the detector 28 as described in method 58. Turning to FIG. 3, in the depicted implementation, the method 58 includes obtaining the material linearization function (e.g., mapping function) or beam hardening projection error for each pixel based on detection coefficients and synthesized water and iodine projections during calibration. The mapping function takes a polynomial form for the water (or water and iodine) and iodine projections. The water and iodine projections to compute the mapping function are synthesized through system modeling, while the water and iodine projections used in the MMC correction described below are obtained from total measured projection and forward projecting the volume of reconstructed images. The modeling process is both accurate and simplistic due to the absence of complex physical phantoms.

In order to obtain the mapping functions, the method 92 includes computing raw projections through $L_w$, which represents the thickness of water, and $L_{io}$, which represents the thickness of iodine. In particular, the method 92 includes computing a total raw projection ($p_t$) 98 of each pixel attenuated by both water and iodine (block 100) in the following equation:

$$p_t = -\log\left(\frac{\sum_E^{kV} S_{kv}(E) \cdot E \cdot e^{-\mu_w(E)L_w - \mu_{io}(E)L_{io}} \cdot \eta(E) \cdot \varepsilon(E)}{\sum_E^{kV} S_{kv}(E) \cdot E \cdot \eta(E) \cdot \varepsilon(E)}\right), \quad (2)$$

where index kv represents the tube voltage at a given detector row location, E represents the photon energy, $S_{kv}(E)$ represents the incident spectrum, $\eta(E)$ represents the scintillator stopping power, $\mu_w(E)$ represents the water mass attenuation coefficient, $\mu_{io}(E)$ represents the iodine mass attenuation coefficient, and $\varepsilon(E)$ represents the detection coefficient. The method 92 also includes computing the effective raw projection ($p_{io}$) 102 of each pixel contributed by iodine (i.e., attenuated by water) in the following equation:

$$p_{io} = -\log\left(\frac{\sum_E^{kV} S_{kv}(E) \cdot E \cdot e^{-\mu_w(E)L_w - \mu_{io}(E)L_{io}} \cdot \eta(E) \cdot \varepsilon(E)}{\sum_E^{kV} S_{kv}(E) \cdot E \cdot e^{-\mu_w(E)L_w} \cdot \eta(E) \cdot \varepsilon(E)}\right). \quad (3)$$

The method 92 also includes computing an effective raw projection ($p_w$) 106 of each pixel contributed by water (i.e., attenuated by iodine) in the following equation:

$$p_w = -\log\left(\frac{\sum_E^{kV} S_{kv}(E) \cdot E \cdot e^{-\mu_w(E)L_w} \cdot \eta(E) \cdot \varepsilon(E)}{\sum_E^{kV} S_{kv}(E) \cdot E \cdot \eta(E) \cdot \varepsilon(E)}\right). \quad (4)$$

Upon obtaining the projections, the method 92 includes spectrally correcting the raw projections 98, 100 for water beam hardening (block 110) to generate a spectrally corrected total projection ($P_t$) attenuated by both water and iodine and a spectrally corrected effective iodine projection ($P_{io}$) 112. In particular, the spectrally corrected total projection ($P_t$) 112 is obtained by the following:

$$P_t = \sum_{n=1}^{NR} a_n p_t^n, \quad (5)$$

where NR represents the beam hardening (BH) order and $a_n$ represents the BH coefficients. The BH order may range from 3 to 5. The spectrally corrected effective iodine projection ($P_{io}$) 112 is obtained by the following:

$$P_{io} = \sum_{n=1}^{NR} a_n p_t^n - \sum_{n=1}^{NR} a_n p_w^n. \quad (6)$$

Due to the beam hardening from iodine, linearity does not hold anymore after spectral correction. That is $$P_t \neq \mu_1 L_w + \mu_2 L_{io} \quad (7)$$

for all the possible combination of ($L_w$, $L_{io}$), where $\mu_1$ and $\mu_2$ are two constants that typically represent the attenuation coefficients at the effective beam energy. In other words, the polychromatic signal ($P_t$) does not equal the sum of the monochromatic signals $\mu_1 L_w$ and $\mu_2 L_{io}$. This non-linearity arising from physics is the root cause of beam hardening in CT images. The mapping functions correct for such non-linearity. The method 92 includes computing the BH error 114 due to iodine (block 116), which is the difference between the sum of the monochromatic signals and the polychromatic signal, as represented by:

$$\Delta p(P_t, P_{io}) = (\mu_1 L_w + \mu_2 L_{io}) - P_t, \quad (8)$$

where $\Delta p(P_t, P_{io})$ represents the BH error 114.

The method 92 includes generating MMC coefficients ($m_{\alpha\beta}$) 118 for each pixel (block 120). The MMC coefficients 118 are obtained through fitting the data pairs $\{(P_t, P_{io}) \Delta p(P_t, P_{io})\}$ generated in equation 8. In other words, the generation of MMC coefficients is based on the BH error 114, the spectrally corrected total raw projection ($P_t$) 112, and the spectrally corrected iodine projection ($P_{io}$) 112. The fitting is applied to each individual detector pixel. Thus, the MMC coefficients 118 already include a self adjustment to correct for BIS artifacts. This eliminates the need for a separate BIS correction step because when MMC is performed, BIS correction is applied automatically.

From simulation, and using the above equations, the method 92 includes capturing the BH error due to iodine as a function of spectrally corrected raw projections (block 122). In particular, the process of capturing the BH error is iterated for $L_w$=0 to 50 cm, step=1 cm, and $L_{io}$=0 to 3 cm, step=0.15 cm, to enable building a functional table 124 of BH error due to iodine against projection values, $P_t$ and $P_{io}$. The BH error is expressed in the following polynomial form:

$$\Delta p(P_t, P_{io}) = \sum_{\alpha=0, \beta=1}^{\alpha=n_1, \beta=n_2} m_{\alpha\beta} P_t^\alpha P_{io}^\beta. \quad (9)$$

In equation (9), $P_t$ and $P_{io}$ are to the $n_1$ and $n_2$ order, respectively, and these are not constant. A rank up to the third order is sufficient for both $n_1$ and $n_2$. From these equations, the mapping functions are obtained that correct for the non-linearity.

After obtaining the material linearization mapping functions, the method 92 includes performing material characterization of an image volume 125 for of a reconstructed image obtained from reconstructing acquired projection data. In particular, the method 92 includes performing material segmentation (block 126) on the image volume 125. Among distinct materials in the human body (e.g., soft tissue, bone, iodine, and metal implants), two different algorithms may be utilized for the material segmentation. The first algorithm may be Hounsfield units (HU) value (e.g., CT value) based, where the different materials are separated based off on designated HU levels and/or ranges representative of each material. The second algorithm may be used for bone tracking, in particular, to separate soft bone from iodine. The method 92 may utilize the first algorithm or both the first and second algorithm for material segmentation. In certain embodiments, the composition of the human body may be segmented into more detailed components such as fat, muscle, stent, calcification, and so forth, which can be integrated into the method 92. In addition, other information may be used to guide segmentation. For example, if the scan is obtained prior to introduction of a contrast agent, input may be provided to the algorithm that iodine is not present in the image. Additionally, pre-contrast agent scans may be used as prior information for post-contrast scan correction. In particular, pre-contrast agent images may provide detailed information on the location and size of the bone region and used to further guide segmentation.

Upon performing material segmentation, the method 92 includes performing inverse basis material decomposition (block 128) on the different segmented projection data. In particular, the inverse basis material decomposition transforms or converts the materials other than iodine and water (i.e., bone and metal) to the basis materials iodine and water. From a physics point of view, neither bone nor metal projections are independent from iodine and metal (and thus the BH error need not be a function of bone and metal projections). Instead, the bone and metal projections are a linear combination of water and iodine from the physics point of view. Thus, the CT values or linear attenuation coefficients can be expressed as the following:

$$\mu_{linear}(\text{bone}) = (m_{bw}\mu_{eff\_mass}(\text{water}) + m_{bio}\mu_{eff\_mass}(\text{iodine})) \cdot D_b \quad (10)$$

and $$\mu_{linear}(\text{metal}) = (m_{mw}\mu_{eff\_mass}(\text{water}) + m_{mio}\mu_{eff\_mass}(\text{iodine})) \cdot D_m, \quad (11)$$

where $\mu_{linear}(\text{bone})$ and $\mu_{linear}(\text{metal})$ represent the effective linear attenuation coefficients of bone and metal, respectively. Also, $\mu_{eff\_mass}(\text{water})$ and $\mu_{eff\_mass}(\text{iodine})$ represent the effective mass attenuation coefficients of water and iodine under a given incident spectrum, respectively. Coefficients $m_{bw}$, $m_{bio}$, $m_{mw}$, and $m_{mio}$ are the material decomposition coefficients of bone and metal onto water and iodine basis, and these coefficients are constants, which only depend on the type of bone and metal. For example, the type of bone and metal may be cortical bone and titanium, respectively. In certain embodiments, if a stent is segmented, its decomposition can also be applied. $D_b$ and $D_m$ are the density values of bone and metal, typically expressed in g/cc, which are converted from the HU values by stripping off their corresponding effective mass attenuation coefficients. As a result of equations (10) and (11), the spectral responses of bone and metal are decomposed into those of water and iodine, which simplifies a complex object by narrowing the BH effects to those of two basis materials, water and iodine.

Alternative to equations (10) and (11), the material decomposition to determine the equivalent iodine fraction from other materials other than iodine may be performed by using the effective keV or using the density of a material to be decomposed. In the effective keV approach, for a voxel identified as material X (let its CT number be $HU_x$) which contains material T and pure material X, the following may be represented as:

$$HU_x = (1-\sigma)HU_T + \sigma HU_{PX}. \quad (12)$$

$HU_T$ represents the CT number for material T, $HU_{PX}$ represents the CT number for the pure material X, and $$\sigma = \frac{HU_x - HU_T}{HU_{PX} - HU_T}. \quad (13)$$

Then, the iodine fraction (expressed by HU) can be computed as $$HU_{xio} \approx m_{xio} \times R \times HU_{PX} \times \frac{HU_x - HU_T}{HU_{PX} - HU_T}, \quad (14)$$

when $$R = \frac{\left(\frac{\mu}{\rho}\right)_{io}(\bar{E})}{\left(\frac{\mu}{\rho}\right)_{PX}(\bar{E})}, \quad (15)$$

where R is a ratio dependent on the selected effective keV ($\bar{E}$) and $m_{xio}$ is the material decomposition factor of material X for iodine, assuming $$\left(\frac{\mu}{\rho}\right)_{PX}(E) = m_{xw}\left(\frac{\mu}{\rho}\right)_w(E) + m_{xio}\left(\frac{\mu}{\rho}\right)_{io}(E). \quad (16)$$

When material T is air, $HU_T = 0$; when material T is water, $HU_T = 1000$. In the approach that uses the density of the material to be decomposed, the iodine fraction can be computed as $$HU_{xio} \approx (HU_{PX} - 1000m_{xw}\rho_{PX}) \times \frac{HU_x - HU_T}{HU_{PX} - HU_T}, \quad (17)$$

where $\rho_{PX}$ is the density for pure material X.

To perform MMC, projections of two materials are need, the total projection (i.e., water and iodine) and the iodine projection (i.e., iodine equivalent portion of the non-water materials). The method 92 includes generating a re-mapped image volume 130 (block 132) for the iodine equivalent portion of each of the non-water materials summed together. The re-mapping process is described in the following equation:

$$V(x,y,z) = D_{iodine}(x,y,z) + m_{bio}D_b(x,y,z) + m_{mio}D_m(x,y,z), \quad (18)$$

where x, y, z represent the Cartesian coordinate of a pixel in the image, V(x,y,z) represents the re-mapped projection for the iodine equivalent portion of each of the non-water materials summed together, and $D_{iodine}(x,y,z)$ represents the value of the segmented pixel identified as iodine solution with water density subtracted.

The method 92 also includes generating a forward projection 134 of the iodine equivalent portion based on the re-mapped projection 130 generated in equation (18) (block 136). The total projection (i.e., water and iodine) can be obtained from the measurement (i.e., spectrally corrected projection 112 ($P_t$)). In certain embodiments, the total projection may be obtained through a forward projection as well. However, only using a single forward projection (i.e., for iodine forward projection 134) speeds up the processing. The remapped image volume 130 is forward-projected using the exact system geometry, and the forward projections are interpolated into the same ray directions, and the same number of views as the measured projections by the detection system, resulting in paired data projections sets.

After obtaining the paired data projections sets, the method 92 includes determining the BH projection error ($\Delta p$) 138 (block 140). As described above, a functional BH error table 124 is generated. The BH projection error 138 (i.e., material linearization function) for each pixel may be obtained from the BH error table 124 via the total projection value (i.e., spectrally corrected total projection 112) and the iodine equivalent forward projection 134 value. The method 92 also includes generating MMC corrected projections 142 for each pixel based on the total projection value (i.e., spectrally corrected total projection 112) and the BH projection error (block 144) as described in the following equation:

$$P_{corr} = P_t + \Delta p. \quad (19)$$

$P_{corr}$ represents the final signal for each pixel to be reconstructed. The correction can be performed in the projection domain or the image domain if the initial image volume and the final volume are both reconstructed with full field of view (FOV). However, in clinical cases, ROI reconstruction is often needed. To obtain the un-truncated forward projection, the initial volume has to be in full FOV, but can be in a reduced matrix. For a reduced matrix, a decimation of 2 in all x-y-z directions is suggested. In other words, it may be preferred that the MMC correction term is added to the original projections to form a new set of corrected projections. The method 92 further includes reconstructing the final MMC corrected image 146 (block 148) from the MMC corrected projections 142.

The initial image volume for each pixel (i.e., projection data 94) may already include HU value contamination from BH and scatter in the initial volume due to the mean value of non-water material not being accurate. This may lead to some inaccuracy in the iodine equivalent projections extracted from forward projecting the re-mapped volume. This may lead to some level of inaccuracy in MMC of a second order. Upon determining if there is sufficient processing time (block 150), the MMC may be reiterated by returning to the material segmentation (block 136) and repeating the remaining process steps, such that more precise iodine projections are obtained from the image volume corrected by the first-pass MMC. If there is no remaining processing time, then reiteration of the process is not performed.

Throughout the above description of methods 58, 92, all the parameters and coefficients are built on physics, as opposed to empirically based techniques, and there are no tuning parameters. In principle, there should be no need for any adjustment to the correction. However, linear scaling factors may be used at various points in the methods 58, 92 to account for any inaccuracies in the modeling. For example, possible tuning places may include scaling forward projected iodine projections to adjust for inaccuracy due to BH in the initial image and scaling the BH error values to adjust for inaccuracy in the beam spectrum modeling.

In another embodiment, each pixel may be characterized or segmented into three basis materials (e.g., water, iodine, and bone). The techniques described above may be used based on the volume fractions of the three basis materials. Thus, for the theoretical calculation of water and iodine, a bone projection may be generated in a similar manner. When using three basis materials, two forward projections may be needed as opposed to a single projection. However, using three basis materials may improve the robustness of the multi-material correction algorithm.

Technical effects of the disclosed embodiments include providing a MMC approach to minimize artifacts in reconstructed images due to beam hardening, heel-effect related spectral variation, and BIS that utilizes a single second-pass correction. In addition, the MMC approach linearizes the detection of all the materials to eliminate beam hardening from its root cause, regardless of the material type. This results in more accurate and consistent CT values of bone, soft tissue, and contrast agent for better clinical diagnosis. Direct clinical benefits of the MMC approach include improved image quality, better differentiation between cysts and metastases, and accurate contrast measurement in CT perfusion.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
acquiring projection data of an object from a plurality of pixels;
reconstructing the acquired projection data from the plurality of pixels into a reconstructed image;
performing material characterization and decomposition of an image volume of the reconstructed image to reduce a number of materials analyzed in the image volume to two basis materials;
generating a re-mapped image volume for at least one basis material of the two basis materials;
performing forward projection on at least the re-mapped image volume for the at least one basis material to produce a material-based projection; and
generating multi-material corrected projections based on the material-based projection and a total projection attenuated by the object, which represents both of the two basis materials, wherein the multi-material corrected projections comprise linearized projections.

2. The method of claim 1, comprising computing a material linearization function for each pixel of the plurality of pixels, wherein the respective material linearization function for each pixel is used to generate the linearized projections.

3. The method of claim 2, wherein computing the material linearization function for each pixel comprises computing for each pixel a total raw projection attenuated by both of the two basis materials and an effective raw projection contributed by the at least one basis material.

4. The method of claim 3, comprising computing for each pixel spectrally corrected raw projections for water beam hardening for both the total raw projection and the effective raw projection contributed by the at least one basis material.

5. The method of claim 3, wherein the total projection attenuated by both of the two basis materials comprises the spectrally corrected total raw projection.

6. The method of claim 3, comprising computing for each pixel a beam hardening error due to the at least one basis material based at least on the spectrally corrected total raw projection.

7. The method of claim 6, comprising generating for each pixel multi-material correction (MMC) coefficients based at least on the beam hardening error, the spectrally corrected total raw projection, and the spectrally corrected effective raw projection contributed by the at least one basis material for the respective pixel.

8. The method of claim 7, wherein the MMC coefficients are self-adjusted to correct for bone-induced spectral artifacts during the generation of the multi-material corrected projections for each pixel.

9. The method of claim 7, comprising determining a detection coefficient for each pixel of a detector for utilization in computing the material linearization function for each pixel.

10. The method of claim 9, comprising generating a table of beam hardening errors for each pixel as a function of the MMC coefficients, the spectrally corrected total raw projection, and the spectrally corrected effective raw projection contributed by the at least one basis material for the respective pixel using an analytical physics model and the detection coefficients.

11. The method of claim 1, wherein performing material characterization of the image volume comprises performing material segmentation of the image volume.

12. The method of claim 1, wherein performing material characterization of the image volume comprises performing inverse basis material decomposition on the image volume to convert materials other than the two basis materials to the two basis materials.

13. The method of claim 1, comprising reconstructing a final multi-material corrected image from the multi-material corrected projections.

14. One or more non-transitory computer-readable media encoding one or more processor-executable routines, wherein the one or more routines, when executed by a processor, cause acts to be performed comprising:
   acquiring projection data of an object from a plurality of pixels;
   reconstructing the acquired projection data from the plurality of pixels into a reconstructed image;
   performing material characterization of an image volume of the reconstructed image to reduce a number of materials analyzed to two basis materials;
   generating a re-mapped image volume for at least one basis material of the two basis materials;
   performing forward projection on at least the re-mapped image volume for the at least one basis material to produce a material-based projection; and
   generating multi-material corrected projections based on the material-based projection and a spectrally corrected total raw projection attenuated by the object, which represents both of the two basis materials, wherein the multi-material corrected projections comprise linearized projections.

15. The one or more non-transitory computer-readable media of claim 14, wherein the one or more-routines, when executed by the processor, cause further acts to be performed comprising:
   computing a material linearization function for each pixel of the plurality of pixels, wherein the respective material linearization function for each pixel is used to generate the linearized projections.

16. The one or more non-transitory computer-readable media of claim 15, wherein the one or more routines, when executed by the processor, cause further acts to be performed comprising:
   computing for each pixel a total raw projection attenuated by both of the two basis materials and an effective raw projection contributed by the at least one basis material when computing the material linearization function for each pixel.

17. The one or more non-transitory computer-readable media of claim 16, wherein the one or more routines, when executed by the processor, cause further acts to be performed comprising:
   computing for each pixel spectrally corrected raw projections for water beam hardening for both the total raw projection and the effective raw projection contributed by the at least one basis material.

18. The one or more non-transitory computer-readable media of claim 16, wherein the one or more routines, when executed by the processor, cause further acts to be performed comprising:
   computing for each pixel a beam hardening error due to the at least one basis material based at least on the spectrally corrected total raw projection.

19. The one or more non-transitory computer-readable media of claim 18, wherein the one or more routines, when executed by the processor, cause further acts to be performed comprising:
   generating for each pixel multi-material correction (MMC) coefficients based at least on the beam hardening error, the spectrally corrected effective raw projection contributed by the at least one basis material for the respective pixel.

20. The one or more non-transitory computer-readable media of claim 19, wherein the one or more routines, when executed by the processor, cause further acts to be performed comprising:
   generating a table of beam hardening errors for each pixel as a function of the MMC coefficients, the spectrally corrected total raw projection, and the spectrally corrected effective raw projection contributed by the at least one basis material for the respective pixel, wherein the MMC coefficients are self-adjusted to correct for bone-induced spectral artifacts during the generation of the multi-material corrected projections for each pixel.

21. The one or more non-transitory computer-readable media of claim 15, wherein the one or more routines, when executed by the processor, cause further acts to be performed comprising:
   performing inverse basis material decomposition on the image volume to convert materials other than the two basis materials to the two basis materials when performing material characterization of the image volume.

22. The one or more non-transitory computer-readable media of claim 15, wherein the one or more routines, when executed by the processor, cause further acts to be performed comprising:
   reconstructing a final multi-material corrected image from the multi-material corrected projections.

23. A system comprising:
   a memory structure encoding one or more processor-executable routines wherein the routines, when executed cause acts to be performed comprising:
   acquiring projection data of an object from a plurality of pixels;
   reconstructing the acquired projection data from the plurality of pixels into a reconstructed image;
   performing material characterization of an image volume of the reconstructed image to reduce a number of materials analyzed to two basis materials;
   generating a re-mapped image volume for at least one basis material of the two basis materials;
   performing forward projection on at least the re-mapped image volume for the at least one basis material to produce an material-based projection; and
   generating multi-material corrected projections based on the material-based projection and a spectrally corrected total raw projection attenuated by the object, which also represents both of the two basis materials, wherein the multi-material corrected projections comprise linearized projections; and a processing component configured to access and execute the one or more routines encoded by the memory structure.

24. The system of claim 23, wherein the routines, when executed by the processor, cause further acts to be performed comprising:
   performing inverse basis material decomposition on the image volume to convert the materials other than the two basis materials to the two basis materials when performing material characterization of the image volume.

25. The system of claim 23, wherein the routines, when executed by the processor, cause further acts to be performed comprising:
   computing for each pixel a beam hardening error due to the at least one basis material based at least on the spectrally corrected total raw projection; and
   generating for each pixel multi-material correction (MMC) coefficients based at least on the beam hardening error, the spectrally corrected total raw projection, and a spectrally corrected raw projection contributed by the at least one basis material for the respective pixel, wherein the MMC coefficients are self-adjusted to correct for bone-induced spectral artifacts during the generation of the multi-material corrected projections for each pixel.

26. A method comprising:
   acquiring projection data of an object from a plurality of pixels;
   reconstructing the acquired projection data from the plurality of pixels into a reconstructed image;
   performing material characterization and decomposition of an image volume of the reconstructed image to reduce a number of materials analyzed in the image volume to two basis materials;
   generating a re-mapped image volume for at least one basis material of the two basis materials;
   performing forward projection on at least the re-mapped image volume for the at least one basis material to produce a material-based projection; and
   generating multi-material corrected projections based on the material-based projection and a total projection attenuated by the object, which represents both of the two basis materials.

* * * * *